(12) United States Patent
Salazar et al.

(10) Patent No.: US 10,864,046 B2
(45) Date of Patent: Dec. 15, 2020

(54) DILATION INSTRUMENT WITH NAVIGATION AND DISTALLY LOCATED FORCE SENSOR

(71) Applicant: Acclarent, Inc., Irvine, CA (US)

(72) Inventors: Henry F. Salazar, Pico Rivera, CA (US); Jetmir Palushi, Irvine, CA (US); David A. Smith, Jr., Lake Forest, CA (US)

(73) Assignee: Acclarent, Inc., Irvine, CA (US)

( * ) Notice: Subject to any disclaimer, the term of this patent is extended or adjusted under 35 U.S.C. 154(b) by 366 days.

(21) Appl. No.: 15/830,205

(22) Filed: Dec. 4, 2017

(65) Prior Publication Data
US 2019/0167351 A1 Jun. 6, 2019

(51) Int. Cl.
*A61B 34/20* (2016.01)
*A61M 25/09* (2006.01)
(Continued)

(52) U.S. Cl.
CPC .............. *A61B 34/20* (2016.02); *A61B 5/062* (2013.01); *A61B 5/066* (2013.01); *A61B 17/24* (2013.01); *A61B 34/25* (2016.02); *A61M 25/09041* (2013.01); *A61M 29/02* (2013.01); *A61B 1/0676* (2013.01); *A61B 1/07* (2013.01); *A61B 34/76* (2016.02); *A61B 2034/105* (2016.02); *A61B 2034/2051* (2016.02); *A61B 2034/2055* (2016.02); *A61B 2034/2059* (2016.02); *A61B 2034/2072* (2016.02); *A61B 2034/2074* (2016.02); *A61B 2034/254* (2016.02);
(Continued)

(58) Field of Classification Search
CPC .......... A61B 17/24; A61M 2025/0681; A61M 2025/1043; A61M 2025/1081; A61M 2029/025; A61M 25/0662; A61M 25/10; A61M 25/104; A61M 29/00; A61M 29/02
See application file for complete search history.

(56) References Cited

U.S. PATENT DOCUMENTS 7,654,997 B2 * 2/2010 Makower ............... A61M 25/10
604/509
7,720,521 B2   5/2010 Chang et al.
(Continued)

OTHER PUBLICATIONS

International Search Report and Written Opinion dated Jun. 7, 2019 for International Application No. PCT/IB2018/059634, 14 pages.

*Primary Examiner* — Ryan J. Severson
(74) *Attorney, Agent, or Firm* — Frost Brown Todd LLC

(57) ABSTRACT

A system includes a dilation catheter and a guide member. The dilation catheter includes a proximal end, a distal end, a dilator, a navigation sensor, and a force sensor. The dilator is positioned proximal to the distal end and is configured to transition between a non-dilated configuration and a dilated configuration. The navigation sensor is positioned distal to the dilator and is configured to cooperate with a guidance system and thereby provide signals indicating a position of the dilation catheter in three-dimensional space. The force sensor is positioned distal to the dilator and is configured to provide signals indicating a force encountered by the force sensor. The dilation catheter is configured to slide relative to the guide member. A distal portion of the guide member is sized and configured to fit in a nasal cavity of a patient.

20 Claims, 10 Drawing Sheets

(51) Int. Cl.
*A61M 29/02* (2006.01)
*A61B 34/00* (2016.01)
*A61B 5/06* (2006.01)
*A61B 17/24* (2006.01)
*A61B 1/06* (2006.01)
*A61G 15/12* (2006.01)
*A61M 3/02* (2006.01)
*A61B 1/07* (2006.01)
*A61B 34/10* (2016.01)
*A61B 90/00* (2016.01)
*A61B 90/30* (2016.01)
*A61M 25/01* (2006.01)

(52) U.S. Cl.
CPC ... *A61B 2090/064* (2016.02); *A61B 2090/306* (2016.02); *A61B 2090/3937* (2016.02); *A61G 15/125* (2013.01); *A61M 3/0295* (2013.01); *A61M 25/0113* (2013.01); *A61M 2205/0216* (2013.01); *A61M 2205/502* (2013.01); *A61M 2210/0618* (2013.01); *A61M 2210/0681* (2013.01)

(56) References Cited

U.S. PATENT DOCUMENTS

| | | | |
|---|---|---|---|
| 7,803,150 B2 * | 9/2010 | Chang | A61M 29/00 604/514 |
| 8,123,722 B2 | 2/2012 | Chang et al. | |
| 8,190,389 B2 | 5/2012 | Kim et al. | |
| 8,277,478 B2 * | 10/2012 | Drontle | A61B 34/20 606/196 |
| 8,282,667 B2 * | 10/2012 | Drontle | A61M 25/0113 606/196 |
| 8,320,711 B2 | 11/2012 | Altmann et al. | |
| 8,702,626 B1 | 4/2014 | Kim et al. | |
| 8,777,926 B2 | 7/2014 | Chang et al. | |
| 8,882,795 B2 * | 11/2014 | Drontle | A61M 29/02 606/199 |
| 8,894,614 B2 * | 11/2014 | Muni | A61B 17/24 604/164.1 |
| 8,986,340 B2 * | 3/2015 | Drontle | A61M 29/02 606/199 |
| 9,095,646 B2 | 8/2015 | Chow et al. | |
| 9,155,492 B2 | 10/2015 | Jenkins et al. | |
| 9,167,961 B2 | 10/2015 | Makower et al. | |
| 9,198,736 B2 | 12/2015 | Kim et al. | |
| 9,463,307 B2 * | 10/2016 | Vaccaro | A61B 34/20 |
| 9,554,817 B2 * | 1/2017 | Goldfarb | A61B 29/00 |
| 9,962,530 B2 * | 5/2018 | Johnson | A61M 29/00 |
| 10,065,028 B2 * | 9/2018 | Liberatore | A61M 25/0136 |
| 10,244,935 B2 * | 4/2019 | Ha | A61B 1/32 |
| 10,363,401 B2 * | 7/2019 | Vaccaro | A61B 17/24 |
| 10,363,402 B2 * | 7/2019 | Drontle | A61M 25/0113 |
| 10,369,337 B2 * | 8/2019 | Drontle | A61M 25/10 |
| 2006/0004323 A1 * | 1/2006 | Chang | A61B 17/24 604/28 |
| 2007/0208252 A1 | 9/2007 | Makower | |
| 2008/0183128 A1 | 7/2008 | Morriss et al. | |
| 2010/0030031 A1 | 2/2010 | Goldfarb et al. | |
| 2011/0004057 A1 | 1/2011 | Goldfarb et al. | |
| 2011/0060214 A1 | 3/2011 | Makower | |
| 2012/0071856 A1 * | 3/2012 | Goldfarb | A61B 17/24 604/514 |
| 2012/0071857 A1 | 3/2012 | Goldfarb et al. | |
| 2012/0078118 A1 * | 3/2012 | Jenkins | A61B 5/065 600/478 |
| 2012/0116210 A1 * | 5/2012 | Zino | A61B 5/6852 600/416 |
| 2014/0074141 A1 | 3/2014 | Johnson et al. | |
| 2014/0200444 A1 | 7/2014 | Kim et al. | |
| 2014/0364725 A1 | 12/2014 | Makower | |
| 2015/0119923 A1 * | 4/2015 | Liberatore | A61B 17/24 606/199 |
| 2016/0008083 A1 | 1/2016 | Kesten et al. | |
| 2016/0270863 A1 * | 9/2016 | Makower | A61B 5/6851 |
| 2016/0287065 A1 * | 10/2016 | Ha | A61B 1/32 |
| 2016/0310042 A1 | 10/2016 | Kesten et al. | |
| 2016/0310714 A1 | 10/2016 | Jenkins et al. | |
| 2017/0056632 A1 * | 3/2017 | Jenkins | A61M 25/0074 |
| 2017/0120019 A1 * | 5/2017 | Goldfard | A61M 25/09041 |
| 2017/0120020 A1 | 5/2017 | Lin et al. | |
| 2018/0104404 A1 * | 4/2018 | Ngo-Chu | A61M 25/0041 |
| 2018/0264237 A1 * | 9/2018 | Palushi | A61M 25/09 |
| 2019/0069959 A1 * | 3/2019 | Palushi | A61B 10/04 |
| 2019/0160268 A1 * | 5/2019 | Ngo-Chu | A61B 1/00195 |
| 2019/0167351 A1 * | 6/2019 | Salazar | A61B 34/20 |
| 2019/0175282 A1 * | 6/2019 | Akbarian | A61B 17/24 |

* cited by examiner

DILATION INSTRUMENT WITH NAVIGATION AND DISTALLY LOCATED FORCE SENSOR

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
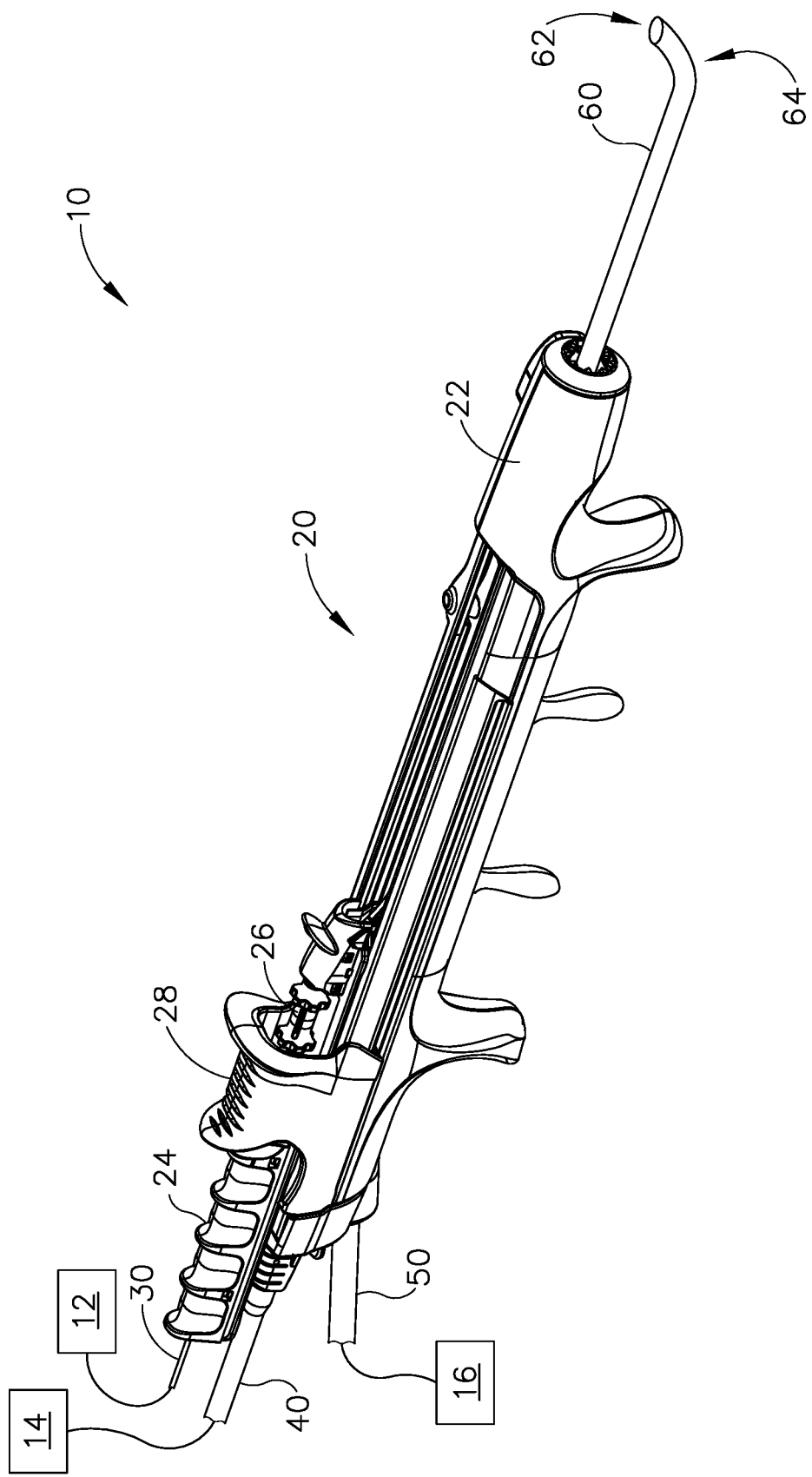
FIG. 1A depicts a perspective view of an exemplary dilation instrument assembly, with a guidewire in a proximal position, and with a dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D shows an exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) comprises a source of light. In some other versions, guidewire power source (12) is part of an IGS system as described below. In the present example, inflation source (14) comprises a source of saline. However, it should be understood that any other suitable source of fluid (liquid or otherwise) may be used. Also in the present example, irrigation fluid source (16) comprises a source of saline. Again, though, any other suitable source of fluid may be used. It should also be understood that flush fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22). It should therefore be understood that dilation instrument (20) may be fully operated by a single hand of a human operator.

A. Exemplary Guide Catheter

A guide catheter (60) extends distally from handle body (22). Guide catheter (60) includes an open distal end (62) and a bend (64) formed proximal to open distal end (62). In the present example, dilation instrument (20) is configured to removably receive several different kinds of guide catheters (60), each guide catheter (60) having a different angle formed by bend (64). These different angles may facilitate access to different anatomical structures. Various examples of angles and associated anatomical structures are described in one or more of the references cited herein; while further examples will be apparent to those of ordinary skill in the art in view of the teachings herein. Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

B. Exemplary Guidewire

Figure 1B:
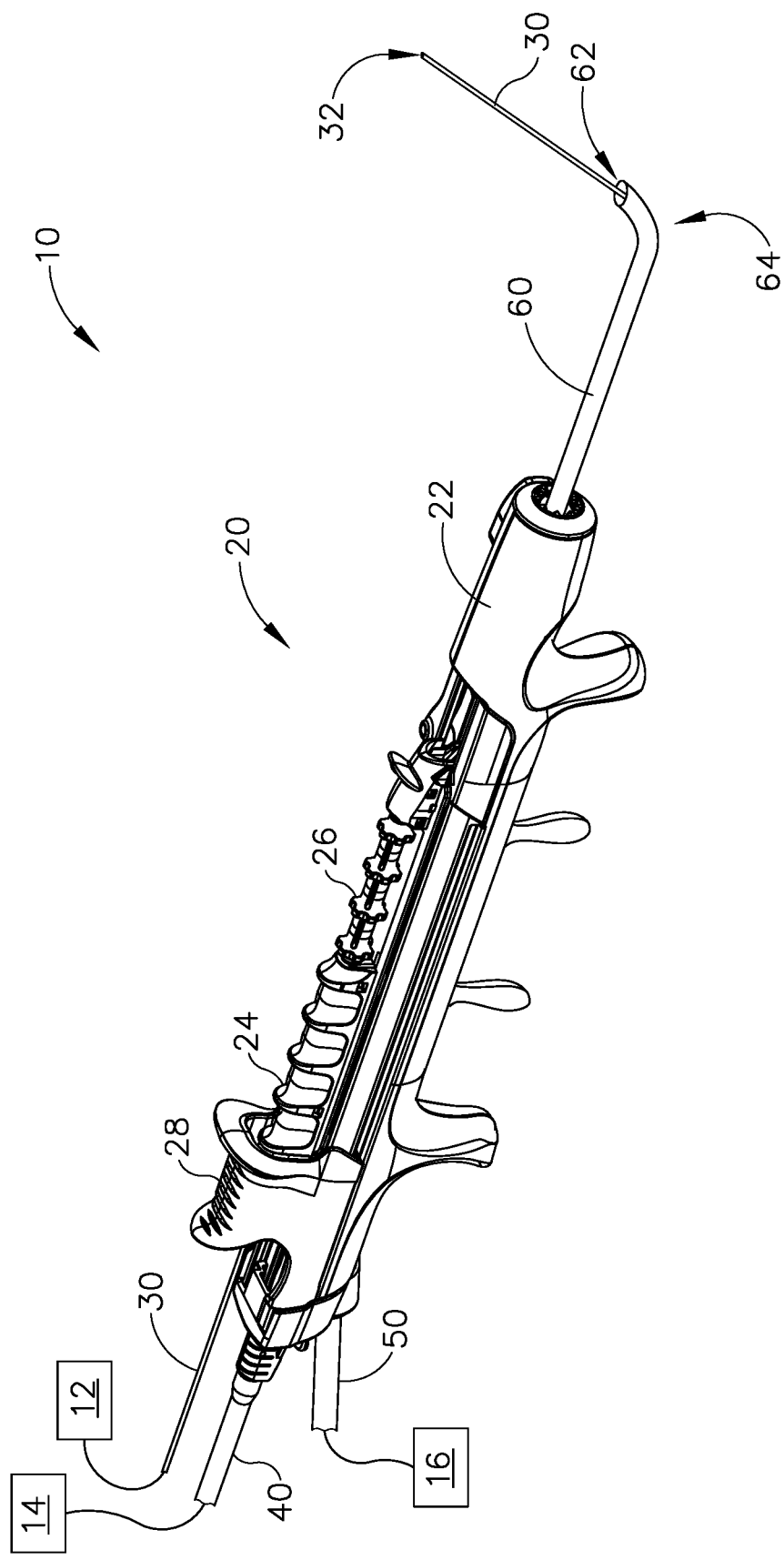
FIG. 1B depicts a perspective view of the dilation instrument assembly of FIG. 1A, with the guidewire in a distal position, and with the dilation catheter in the proximal position.

Dilation instrument (30) further comprises a guidewire (30), which is coaxially disposed in guide catheter (60). Guidewire slider (24) is secured to guidewire (30) such that translation of guidewire slider (24) relative to handle body (22) provides corresponding translation of guidewire (30) relative to handle body (22). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, guidewire (30) includes a preformed bend formed just proximal to the distal end (32) of guidewire (30). In such versions, the preformed bend and the rotatability provided via guidewire spinner (26) may facilitate alignment and insertion of distal end (32) into a sinus ostium, Eustachian tube, or other passageway to be dilated. Also in some versions, guidewire (30) includes at least one optical fiber extending to a lens or other optically transmissive feature in distal end (32). This optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure.

By way of example only, guidewire (30) may be configured in accordance with at least some of the teachings of U.S. Pat. No. 9,155,492, the disclosure of which is incorporated by reference herein. In some versions, guidewire (30) is configured similar to the Relieva Luma Sentry™ Sinus Illumination System by Acclarent, Inc. of Irvine, Calif. In addition to, or as an alternative to, including one or more optical fibers, guidewire (30) may include a sensor and at least one wire that enables guidewire (30) to provide compatibility with an IGS system as described in greater detail below. Other features and operabilities that may be incorporated into guidewire (30) will be apparent to those of ordinary skill in the art in view of the teachings herein.

C. Exemplary Dilation Catheter

Figure 1C:
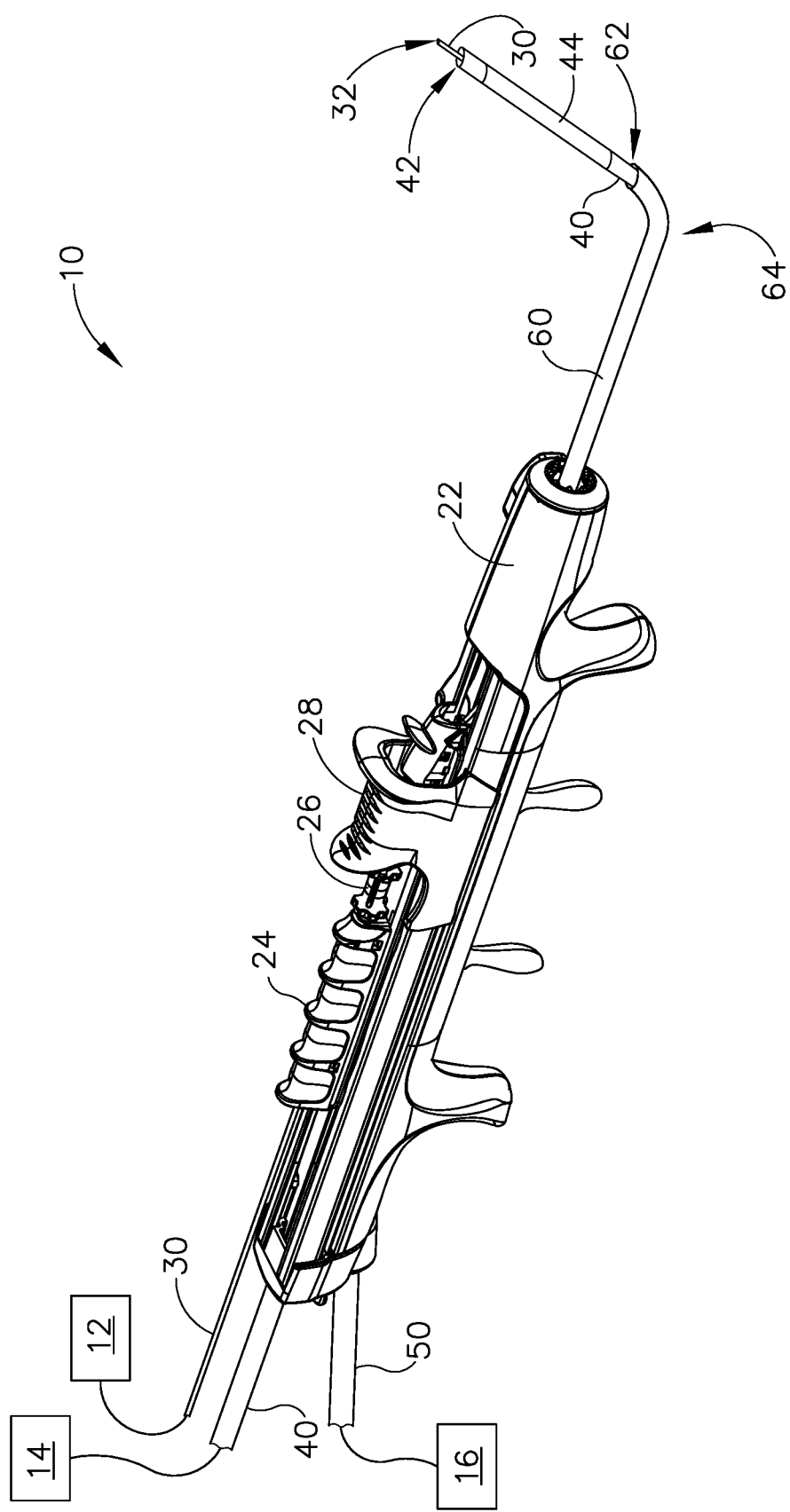
FIG. 1C depicts a perspective view of the dilation instrument assembly of FIG. 1A, with the guidewire in a distal position, with the dilation catheter in a distal position, and with a dilator of the dilation catheter in a non-dilated state.

Dilation instrument (30) further comprises a dilation catheter (40), which is coaxially disposed in guide catheter (60). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (62) of guide catheter (60). As can also be seen in FIG. 1C, a distal portion of guidewire (30) protrudes distally from the open distal end of dilation catheter (40) when guidewire (30) and dilation catheter are both in distal positions.

Figure 1D:
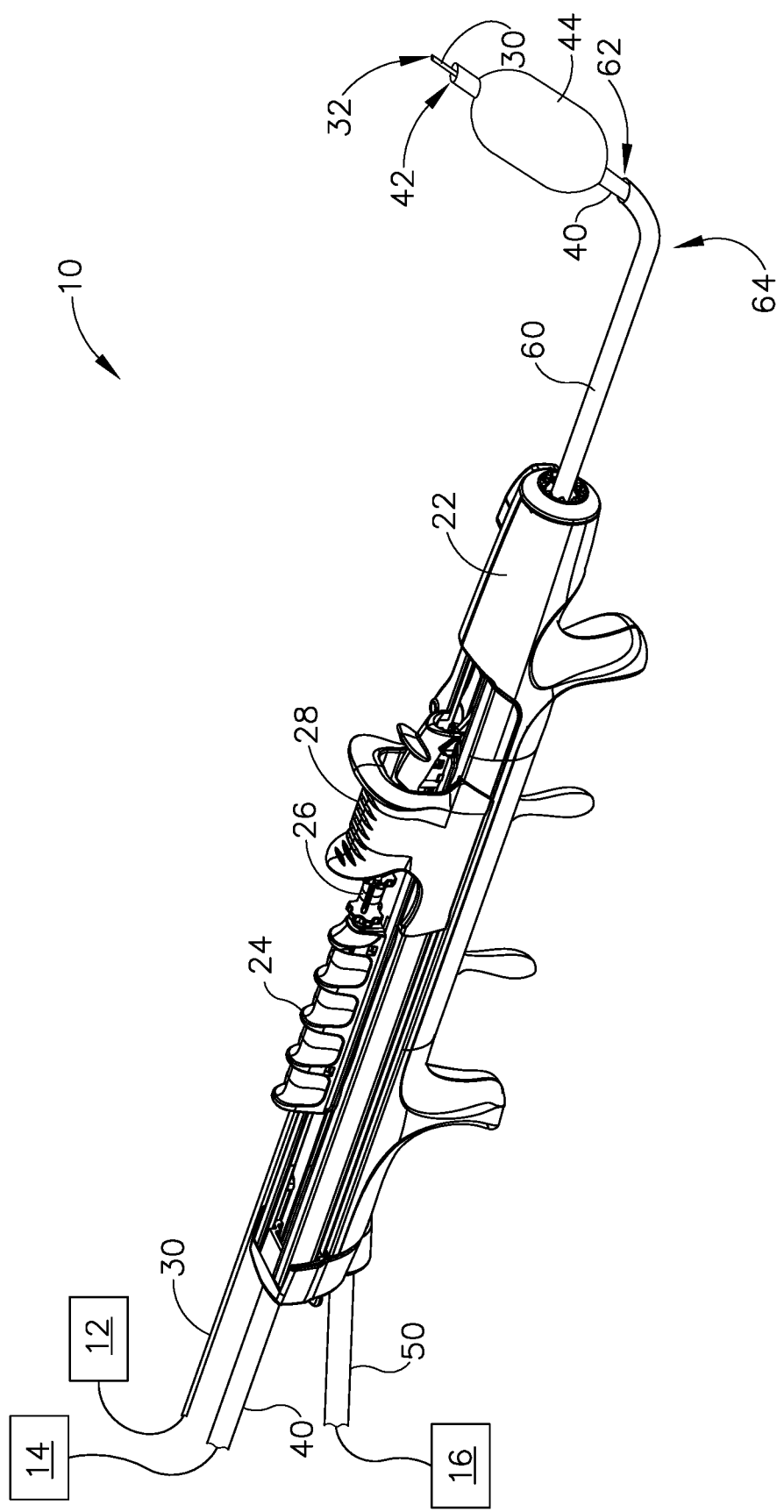
FIG. 1D depicts a perspective view of the dilation instrument assembly of FIG. 1A, with the guidewire in a distal position, with the dilation catheter in the distal position, and with a dilator of the dilation catheter in a dilated state.

Dilation catheter (40) of the present example comprises a non-extensible balloon (44) located just proximal to open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In some versions, inflation source (14) comprises a manually actuated source of pressurized fluid. In some such versions, the manually actuated source of pressurized fluid is configured and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein. Other suitable configurations that may be used to provide a source of pressurized fluid will be apparent to those of ordinary skill in the art in view of the teachings herein.

While not shown, it should be understood that dilation catheter (40) may include at least two separate lumens that are in fluid isolation relative to each other. One lumen may provide a path for fluid communication between balloon (44) and inflation source (14). The other lumen may provide a path to slidably receive guidewire (30).

While dilation catheter (40) of the present example is configured to transition between a non-dilated state and a dilated state based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar to the Relieva Ultirra® Sinus Balloon Catheter by Acclarent, Inc. of Irvine, Calif. In some other versions, dilator catheter (40) is configured and operable similar to the Relieva Solo Pro™ Sinus Balloon Catheter by Acclarent, Inc. of Irvine, Calif. Other suitable variations of dilation catheter (40) will be apparent to those of ordinary skill in the art in view of the teachings herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, Calif. Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, Calif.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned. Of course, irrigation may be provided in the absence of a dilation procedure; and a dilation procedure may be completed without also including irrigation. It should therefore be understood that dilation fluid source (16) and tube (50) are merely optional.

E. Exemplary Variations

In the present example, guidewire (30) is coaxially disposed within dilation catheter (40), which is coaxially disposed within guide catheter (60). In some other versions, guide catheter (60) is omitted from dilation instrument (20). In some such versions, a malleable guide member is used to guide guidewire (30) and dilation catheter (40). In some such versions, guidewire (30) is omitted and dilation catheter (40) is slidably disposed about the exterior of the internal malleable guide member. In some other versions, guidewire (30) is slidably disposed about the exterior of the internal malleable guide member; and dilation catheter (40) is slidably disposed about the exterior of guidewire (30). In still other versions, guidewire (30) is slidably disposed within the interior of the malleable guide member; and dilation catheter (40) is slidably disposed about the exterior of the malleable guide member.

By way of example only, versions of dilation instrument (20) that include a malleable guide member may be constructed and operable in accordance with at least some of the teachings of U.S. Pub. No. 2016/0310714, entitled "Balloon Dilation System with Malleable Internal Guide," published Oct. 27, 2016, issued as U.S. Pat. No. 10,137,285 on Nov. 27, 2018, the disclosure of which is incorporated by reference herein. As another merely illustrative example, versions of dilation instrument (20) that include a malleable guide member may be constructed and operable in accordance with at least some of the teachings of U.S. patent application Ser. No. 14/928,260, entitled "Apparatus for Bending Malleable Guide of Surgical Instrument," filed Oct. 30, 2015, issued as U.S. Pat. No. 10,137,286 on Nov. 27, 2018, the disclosure of which is incorporated by reference herein; and/or U.S. Pub. No. 2012/0071857, entitled "Methods and Apparatus for Treating Disorders of the Sinuses," published Mar. 22, 2012, now abandoned, the disclosure of which is incorporated by reference herein.

It should be understood that the variations of dilation instrument (20) described below in the context of an IGS system may be incorporated into versions of dilation instrument (20) having a malleable guide just like the variations of dilation instrument (20) described below in the context of an IGS system may be incorporated into versions of dilation instrument (20) having a rigid guide catheter (60).

Various examples below describe the use of an IGS system to provide navigation of instruments within a patient. In particular, various examples below describe how dilation instrument assembly (10) may be modified to incorporate IGS system features. However, it should also be understood that dilation instrument assembly (10) may be used in conjunction with conventional image guidance instruments, in addition to being used with IGS system components. For instance, dilation instrument assembly (10) may be used in conjunction with an endoscope, at least to provide initial positioning of guide catheter (60) in a patient. By way of example only, such an endoscope may be configured in accordance with at least some of the teachings of U.S. Pub. No. 2010/0030031, now abandoned, the disclosure of which is incorporated by reference herein. Other suitable kinds of endoscopes that may be used with the various versions of dilation instrument assembly (10) described herein will be apparent to those of ordinary skill in the art.

Other exemplary dilation catheter systems that may be used include the systems described in U.S. Pat. Nos. 8,777, 926 and 9,095,646, the disclosures of which are incorporated by reference herein; and the Relieva Ultirra® Sinus Balloon Catheter system by Acclarent, Inc. of Irvine, Calif.

II. Exemplary Image Guided Surgery Navigation System

Figure 2:
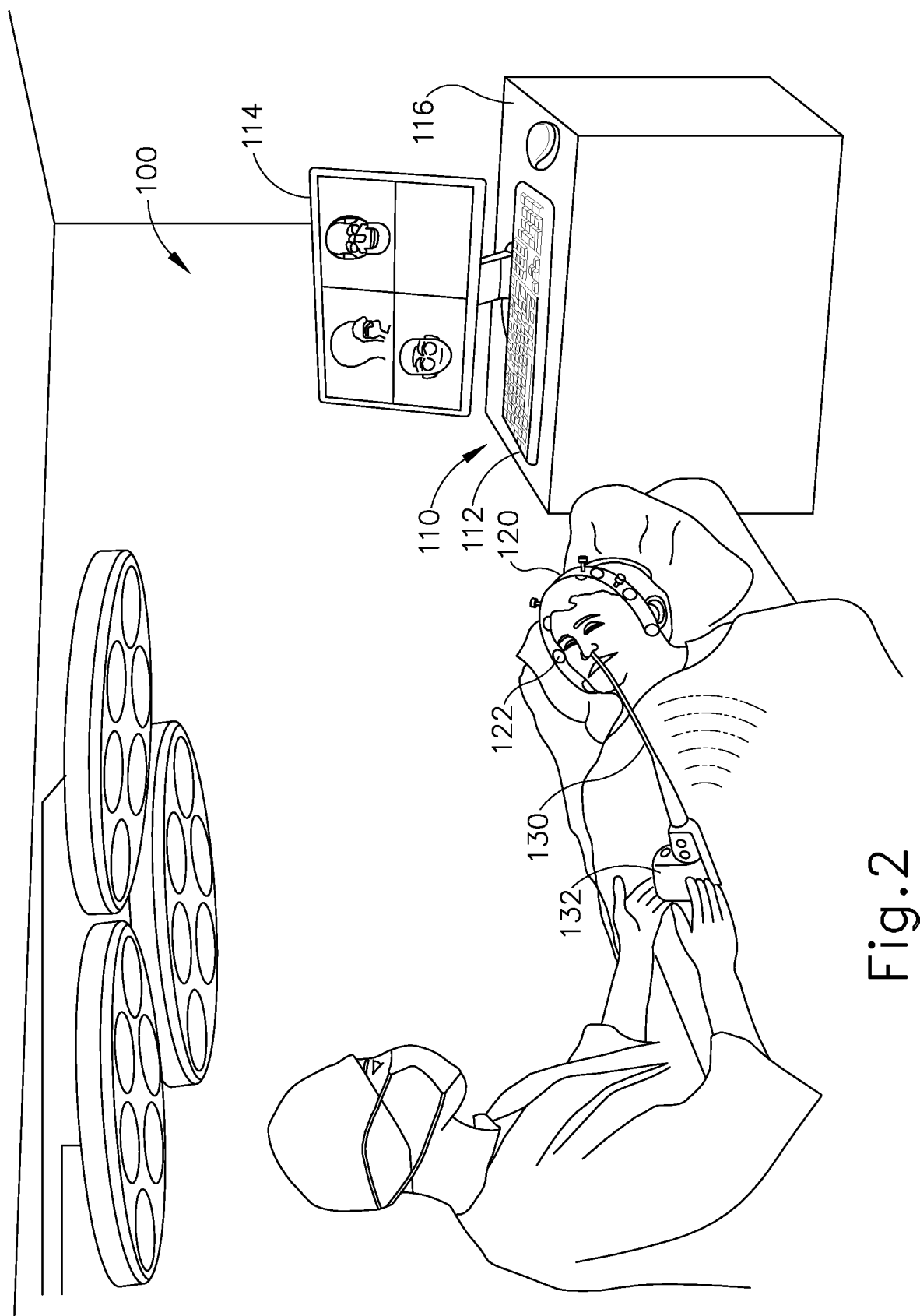
FIG. 2 depicts a schematic view of an exemplary sinus surgery navigation system.

FIG. 2 shows an exemplary GS navigation system (100) whereby an ENT procedure may be performed using GS. In some instances, GS navigation system (100) is used during a procedure where dilation instrument assembly (10) that may be used to dilate the ostium of a paranasal sinus; or to dilate some other anatomical passageway (e.g., within the ear, nose, or throat, etc.). However, it should be understood that GS navigation system (100) may be readily used in various other kinds of procedures.

In addition to or in lieu of having the components and operability described herein GS navigation system (100) may be constructed and operable in accordance with at least some of the teachings of U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein; U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, GS navigation system (100) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

Figure 3:
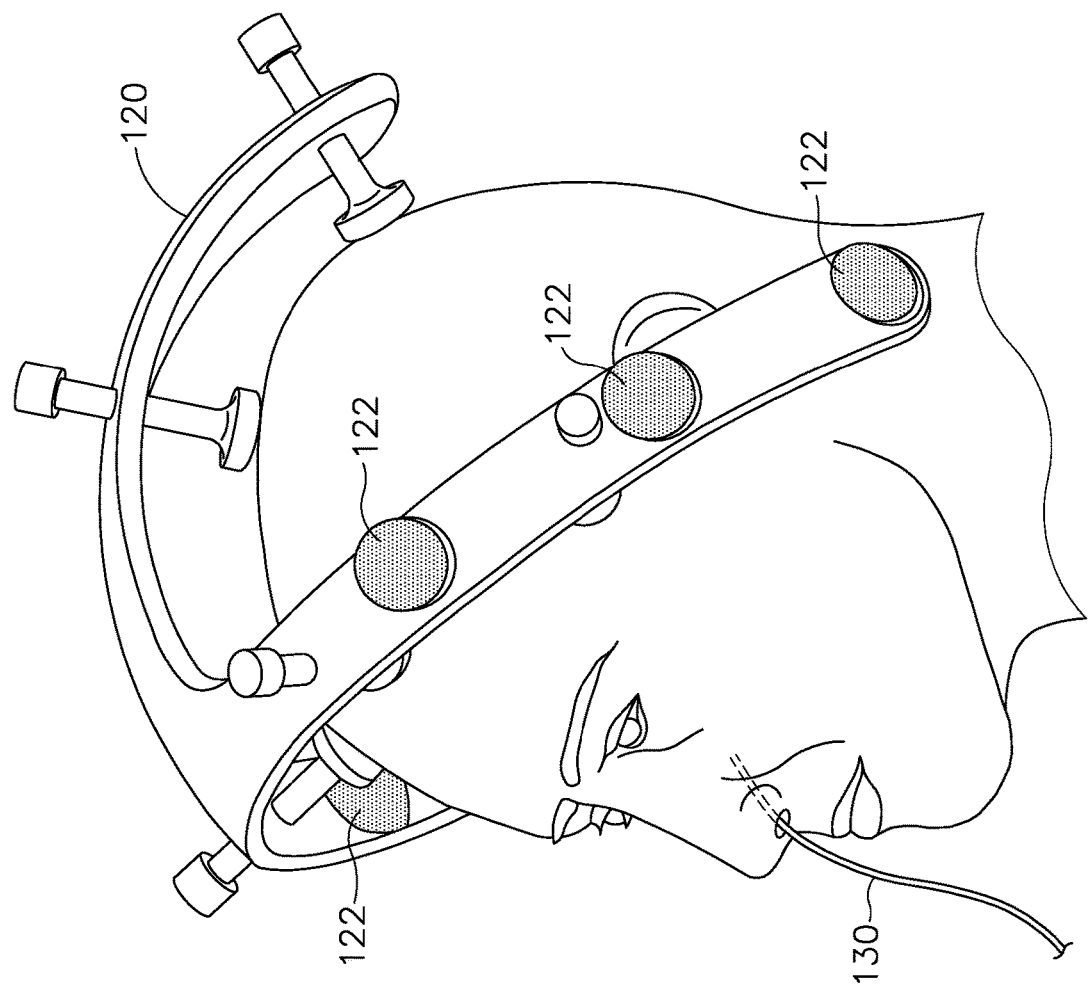
FIG. 3 depicts a perspective view of the head of a patient, with components of the navigation system of FIG. 2.

GS navigation system (100) of the present example comprises a set of magnetic field generators (122). Before a surgical procedure begins, field generators (122) are fixed to the head of the patient. As best seen in FIG. 3, field generators (122) are incorporated into a frame (120), which is clamped to the head of the patient. While field generators (122) are secured to the head of the patient in this example, it should be understood that field generators (122) may instead be positioned at various other suitable locations and on various other suitable structures. By way of example only, field generators (122) may be mounted on an independent structure that is fixed to a table or chair on which the patient is positioned, on a floor-mounted stand that has been locked in position relative to the head of the patient, and/or at any other suitable location(s) and/or on any other suitable structure(s).

Field generators (122) are operable to generate an electromagnetic field around the head of the patient. In particular, field generators (122) are operated so as to transmit alternating magnetic fields of different frequencies into a region in proximity to frame (120). Field generators (122) thereby enable tracking of the position of a navigation guidewire (130), or navigation dilation catheter (140), that is inserted into a nasal sinus of the patient and in other locations within the patient's head. Various suitable components that may be used to form and drive field generators (122) will be apparent to those of ordinary skill in the art in view of the teachings herein.

Navigation guidewire (130) may be used as a substitute for guidewire (30) described above, and may include a sensor (not shown) that is responsive to movement within the fields generated by field generators (122). In particular, signals generated by the sensor of navigation guidewire (130) may be processed by processor (110) to determine the three-dimensional location of navigation guidewire (130) within the patient. Various suitable forms that the sensor may take will be apparent to those of ordinary skill in the art in view of the teachings herein, particularly in view of several of the references that are cited herein in the context of GS navigation system (100). It should be understood that, when used as a substitute for guidewire (30) in dilation instrument assembly (10), navigation guidewire (130) may facilitate navigation of instrumentation of dilation instrument assembly (10) within the patient during performance of a procedure to dilate the ostium of a paranasal sinus; or to dilate some other anatomical passageway (e.g., within the ear, nose, or throat, etc.). It should also be understood that other components of dilation instrument assembly (10) may incorporate a sensor like the sensor of navigation guidewire (130), including but not limited to the exemplary alternative dilation catheter (140) described below.

GS navigation system (100) of the present example further comprises a processor (110), which controls field generators (122) and other elements of GS navigation system (100). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Console (116) also connects to other elements of system (100). For instance, as shown in FIG. 2 a coupling unit (132) is secured to the proximal end of navigation guidewire (130). Coupling unit (132) of this example is configured to provide wireless communication of data and other signals between console (116) and navigation guidewire (130). In some versions, coupling unit (132) simply communicates data or other signals from navigation guidewire (130) to console (116) uni-directionally, without also communicating data or other signals from console (116). In some other versions, coupling unit (132) provides bidirectional communication of data or other signals between navigation guidewire (130) to console (116). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Processor (110) uses software stored in a memory of processor (110) to calibrate and operate system (100). Such operation includes driving field generators (122), processing data from navigational guidewire (130), processing data from operating controls (112), and driving display screen (114). The software may be downloaded to processor (110) in electronic form, over a network, for example, or it may, alternatively or additionally, be provided and/or stored on non-transitory tangible media, such as magnetic, optical, or electronic memory.

Processor (110) is further operable to provide video in real time via display screen (114), showing the position of the distal end of navigational guidewire (130) in relation to a video camera image of the patient's head, a CT scan image of the patient's head, and/or a computer generated three-dimensional model of the anatomy within and adjacent to the patient's nasal cavity. Display screen (114) may display such images simultaneously and/or superimposed on each other. Moreover, display screen (114) may display such images during the surgical procedure. Such displayed images may also include graphical representations of instruments that are inserted in the patient's head, such as navigational guidewire (130), such that the operator may view the virtual rendering of the instrument at its actual location in real time. Such graphical representations may actually look like the instrument or may be a much simpler representation such as a dot, crosshairs, etc. By way of example only, display screen (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head.

In the present example, navigational guidewire (130) includes one or more coils at the distal end of navigational guidewire (130). Such a coil serves as a sensor as referred to above. When such a coil is positioned within an electromagnetic field generated by field generators (122), movement of the coil within that magnetic field may generate electrical current in the coil, and this electrical current may be communicated along the electrical conduit(s) in navigational guidewire (130) and further to processor (110) via coupling unit (132). This phenomenon may enable IGS navigation system (00) to determine the location of the distal end of navigational guidewire (130) within a three-dimensional space as will be described in greater detail below. In particular, processor (110) executes an algorithm to calculate location coordinates of the distal end of navigational guidewire (130) from the position related signals of the coil(s) in navigational guidewire (130).

In some instances, navigational guidewire (130) is used to generate a three-dimensional model of the anatomy within and adjacent to the patient's nasal cavity; in addition to being used to provide navigation for dilation catheter system (100) within the patient's nasal cavity. Alternatively, any other suitable device may be used to generate a three-dimensional model of the anatomy within and adjacent to the patient's nasal cavity before navigational guidewire (130) is used to provide navigation for dilation catheter system (100) within the patient's nasal cavity. By way of example only, a model of this anatomy may be generated in accordance with at least some of the teachings of U.S. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (116). Console (116) may thus render images of at least a portion of the model via display screen (114) and further render real-time video images of the position of navigational guidewire (130) in relation to the model via display screen (114).

III. Exemplary Support Assembly for Navigation System Components

Some medical procedures, including but not limited to medical procedures that are performed in the ear, nose, or throat of a patient (referred to herein as "ENT procedures"), may be performed while the patient is supported by a chair. As shown in FIGS. 2-3, when an ENT procedure is performed with the assistance of an IGS navigation system (100), it may be necessary to position an array of field generators (122) around the patient's head. In the example described above, field generators (122) are mounted to a frame (120), which is mounted to the patient's head. It may be desirable to instead position field generators (122) on a support structure that is not mounted to the patient's head. For instance, when the patient is seated in a chair, it may be desirable to have the field generators (122) supported by the structure of the chair rather than being supported by the patient's head.

Conventional medical procedure chairs, including those designed particularly for use in ENT procedures, may include several metallic components in the headrest of the chair. While such headrests may provide adequate structural support for field generators (122), metallic components in such headrests (and/or elsewhere within the chair) may interfere with the functioning or accuracy of IGS navigation system (100) if the metallic components are too close to field generators (122). It may therefore be desirable to rely on the chair to structurally support field generators (122) while avoiding the risk of metallic features of the chair compromising the functioning or accuracy of IGS navigation system (100). Moreover, it may be desirable to provide a field generator (122) support assembly that may be readily retrofitted to a conventional medical procedure chair, such that a consumer need not purchase an entire new chair in order to obtain the support functionality described above. In versions where the support assembly may be retrofitted to a conventional medical procedure chair, it may be desirable to enable an operator to accomplish such retrofitting without requiring the use of tools such as screwdrivers, etc.

The following examples relate to support assemblies that may be retrofitted to a conventional medical procedure chair, relying on the chair itself (rather than the patient's head) to structurally support IGS navigation system (100) components such as field generators (122), without the risk of any metallic components of the chair interfering with the functioning or accuracy of IGS navigation system (100), and without requiring the use of separate tools in order to complete the retrofitting.

Figure 4:
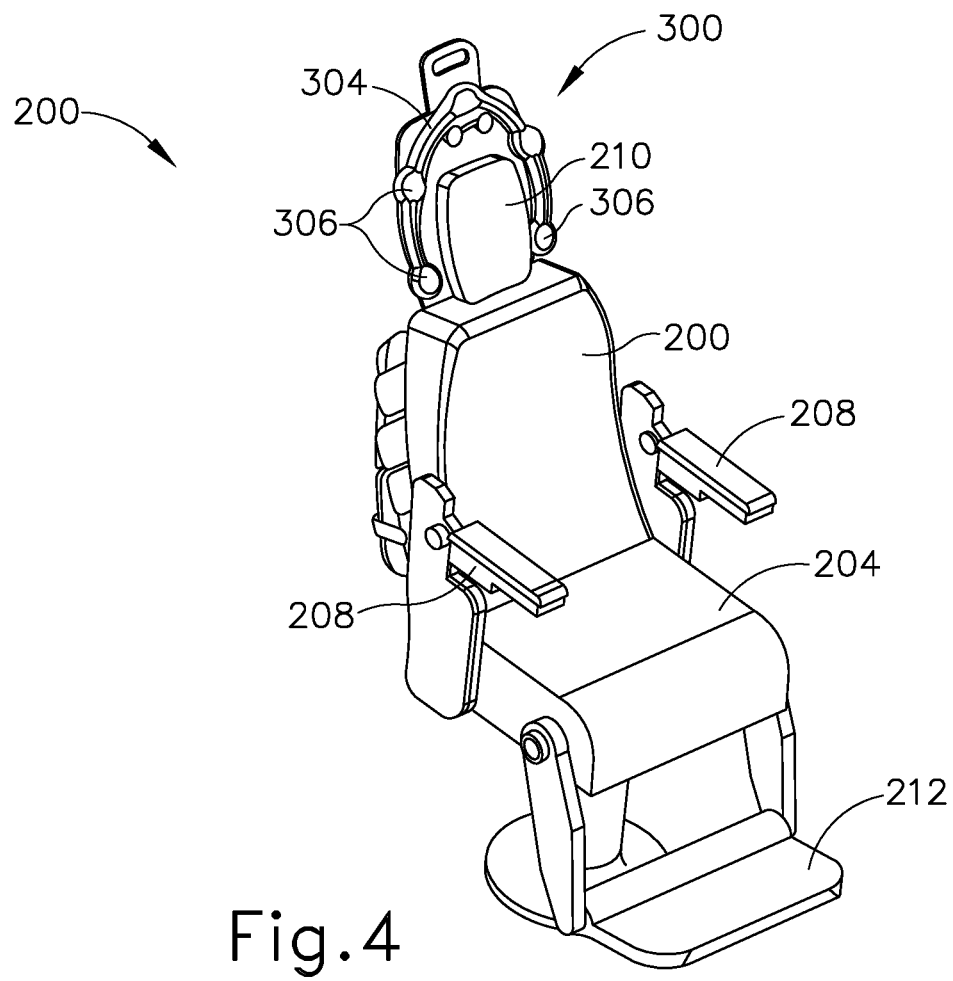
FIG. 4 depicts a perspective view of an exemplary medical procedure chair, with an exemplary navigation component support assembly secured to the chair.
Figure 5:
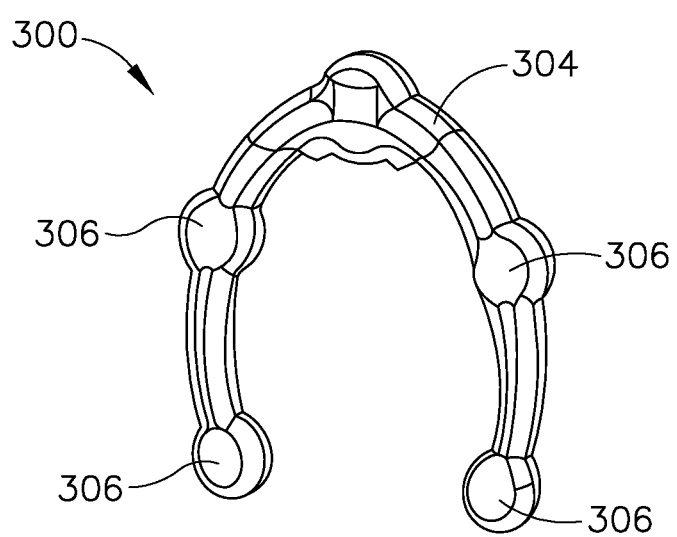
FIG. 5 depicts a perspective view of the navigation component support assembly of FIG. 4.

FIG. 4 shows an exemplary ENT procedure chair (200) with a support assembly (300) mounted thereon and supporting a navigation system component (400). Chair (200) includes a base (202), a bottom support (204), a backrest (206), a pair of armrests (208), a headrest (210) and a footrest (212). Chair (200) is configured to seat a patient thereon such that support assembly (300) is positioned adjacent to the patient's head. In particular, headrest (210) is configured to support the head of a patient while the patient is seated on bottom support (204). Support assembly (300) of this example includes a wedge-shaped body (301) that is configured to rest against a front surface (not shown) of backrest (206). A frame (304) extends from and is secured to backrest (206). As best seen in FIG. 5, frame (304) is generally shaped like a horseshoe in this example and includes a plurality of integral field generators (306). Field generators (306) of this example are configured and operable just like field generators (122) described above.

Frame (304) is configured to hold field generators (306) in a generally horseshoe-shaped arrangement about the head of the patient, without frame (304) contacting the patient's head. A cable (not shown) is in communication with field generators (306) and thereby provides a conduit for communication between field generators (306) and processor (110) of IGS navigation system (100). Various features that may be used to secure support assembly (300) to backrest (206) will be apparent to those of ordinary skill in the art in view of the teachings herein.

IV. Navigation and Force Sensing Dilation Catheter

In the example described above, with field generators (306) mounted to frame (304) and assembled to chair (200), it may be desirable to employ an alternative dilation catheter in lieu of dilation catheter (40) described above. In particular, it may be desirable to use a variation of dilation catheter (40) that is configured and operable to provide real-time navigational data as the dilation catheter is advanced into the paranasal sinus or some other anatomical passageway of a patient (e.g., within the ear, nose, or throat, etc.). Providing a dilation catheter that may be used to dilate an anatomical passageway while generating live feedback of the current location of the instrument may be beneficial to aid an operator in guiding the instrument to the target site during various kinds of procedures. Incorporating navigation system components, such as sensors, onto the dilation catheter that are configured to communicate with IGS navigation system (100) described above may be desirable to accurately observe the position of the dilation catheter within the patient's head.

Incorporating force sensing components, through additional sensors, onto the variation of dilation catheter (40) may be further desirable to observe the force and/or resistance encountered by the dilation catheter as it is advanced through the anatomical passageway. In unison, the combination of a navigation system sensor(s) and a force sensing sensor(s) on/in the dilation catheter may be beneficial to provide an operator with live feedback that the operator may use to adjust their manipulation of the instrument.

The following description provides various examples of a dilation catheter that incorporates navigation system components and force sensing components that are configured to cooperatively communicate with IGS navigation system (100) to improve tracking the position of an instrument that is inserted into a nasal cavity of the patient and in other locations within the patient's head. The navigation system and force sensing components are configured to be responsive to movement of the dilation catheter in relation to the fields generated by field generators (306) such that the signals generated by the instrument sensors may be processed by a processor to accurately determine the three-dimensional location of the instrument within the patient.

It should be understood that the navigation system and force sensing components described below may be readily used in conjunction with any of the various navigation systems (100) and support assemblies (300) described above and in any of the various surgical procedures described in the various references described herein. Other suitable ways in which the below-described navigation system components may be used will be apparent to those of ordinary skill in the art in view of the teachings herein.

Figure 6:
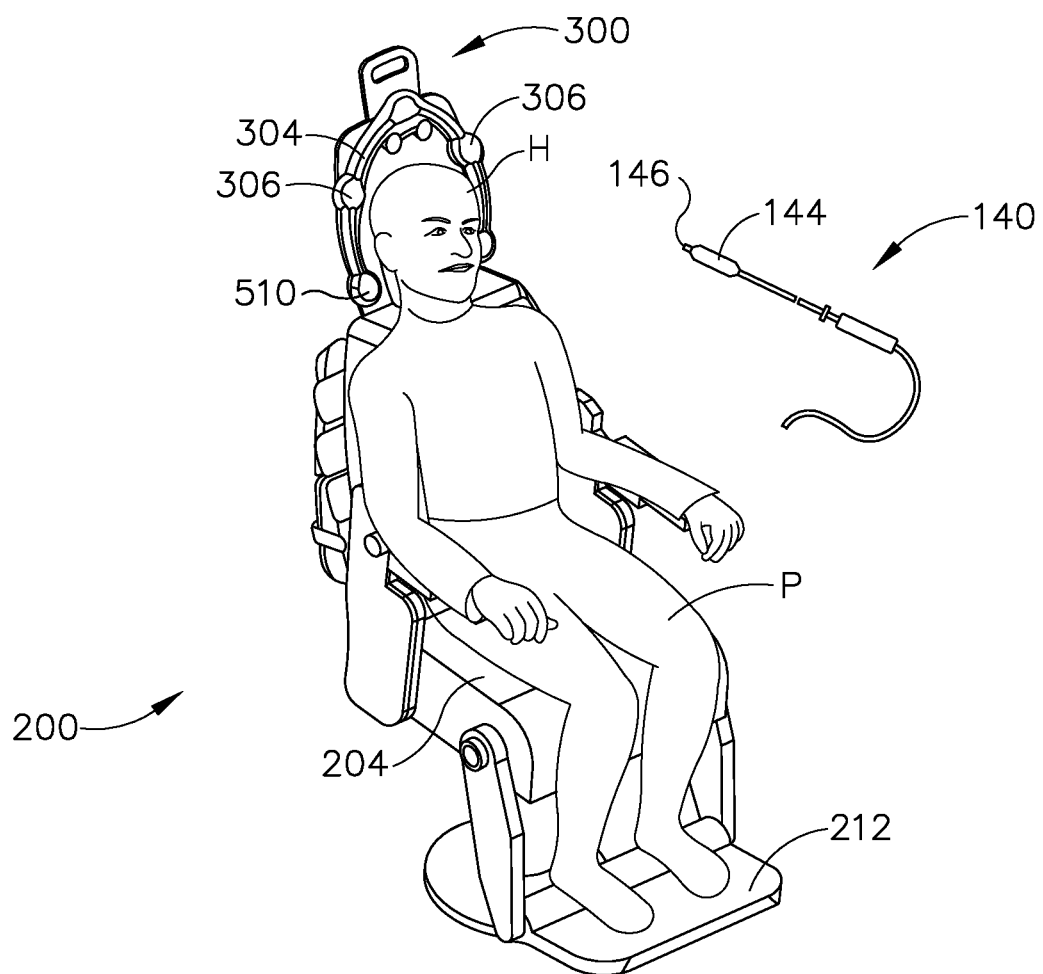
FIG. 6 depicts the medical procedure chair of FIG. 4, with a representation of a patient seated in the chair, and with an exemplary alternative dilation catheter advanced toward the patient.
Figure 7:
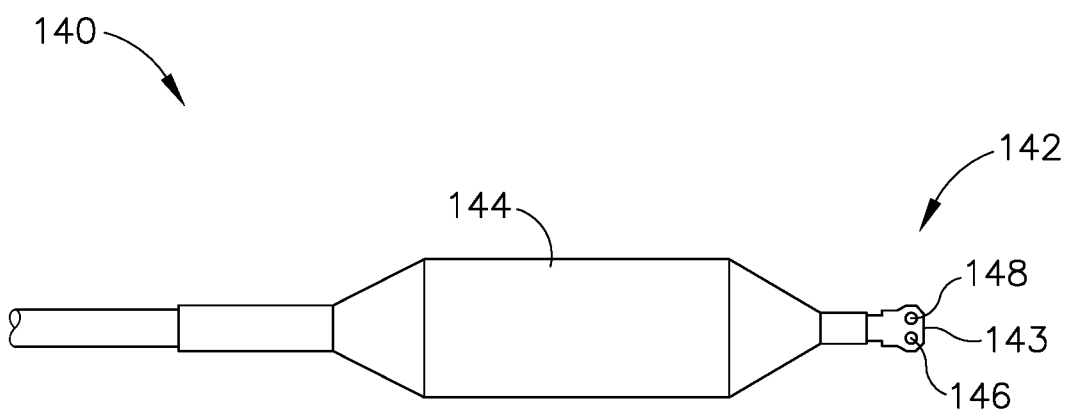
FIG. 7 depicts a side elevational view of the distal portion of the dilation catheter of FIG. 6, including a navigation sensor and a force sensor.

FIG. 6 shows a diagrammatic representation of a patient (P) seated on ENT procedure chair (200) as described above, with a head (H) of patient (P) supported by headrest (342). In particular, head (H) of patient (P) is situated adjacent to support assembly (300) such that the horseshoe-shaped frame (304) extends about head (H) of patient (P) without any field generator (306) contacting head (H) of patient (P). FIG. 6 further shows an exemplary alternative dilation catheter (140) that may be used as a substitute for dilation catheter (40) described above. As best seen in FIG. 7, dilation catheter (140) comprises a balloon (144) and a navigation sensor (146) proximate to a distal end (142) of dilation catheter (140). Except as otherwise described below, dilation catheter (140), balloon (144), and navigation sensor (146) are configured and operable just like dilation catheter (40), balloon (44), and navigation sensor (136), respectively, described above. It should be understood that dilation catheter (140) of the present example may be readily incorporated into system (100) described above. It should also be understood that, in many respects, dilation catheter (140) functions substantially similar to dilation catheter (40) described above, such that dilation catheter (140) is operable to be used in dilation instrument assembly (10) and thus be coaxially received within guide catheter (30).

In the present example, navigation sensor (146) is positioned along a portion of distal end (142), distally relative to balloon (144) and proximally relative to a tip end (143) of distal end (142). In this instance, navigation sensor (146) is configured to be responsive to movement within the fields generated by field generators (122). In particular, signals generated by navigation sensor (146) of dilation catheter (140) may be processed by processor (110) to determine the three-dimensional location of dilation catheter (140) within the patient. Various suitable forms that navigation sensor (146) may take will be apparent to those of ordinary skill in the art in view of the teachings herein, particularly in view of several of the references that are cited herein in the context of IGS navigation system (100). As will be described in greater detail below, an alternate processor (150) may be used to process the signals generated by navigation sensor (146) to determine the three-dimensional location of dilation catheter (140) while simultaneously processing signals generated by a force sensor (148) to determine an amount of force applied against distal end (142) of dilation catheter (140).

In the present example, dilation catheter (140) includes one or more coils at distal end (142), with the one or more coils serving as sensor (146) as referred to above. For instance, navigation sensor (146) may comprise one or more conductive coils of wire, with at least one such coil being wrapped about the longitudinal axis of dilation catheter (140). When such a coil is positioned within an electromagnetic field generated by field generators (122, 306), movement of the coil within that magnetic field may generate electrical current in the coil, and this electrical current may be communicated along the electrical conduit(s) in dilation catheter (140) and further to processor (150) via coupling unit (152). This phenomenon may enable system (160) to determine the location of distal end (142) of dilation catheter (140) within a three-dimensional space as will be described in greater detail below. In particular, processor (150) executes an algorithm to calculate location coordinates of distal end (142) from the position related signals of the coil(s) in dilation catheter (140). Alternatively, sensor (146) may be comprised of other similar imaging modalities. By way of example only, sensor (146) includes an x-ray, electromagnetic, radio-frequency, ultrasound, radiation, optics, etc., or other various suitable modalities as will be apparent to those of ordinary skill in the art.

When used as a substitute for dilation catheter (40) in dilation instrument assembly (10), dilation catheter (140) may facilitate navigation of instrumentation of dilation instrument assembly (10) within the patient during performance of a procedure to dilate the ostium of a paranasal sinus; or to dilate some other anatomical passageway (e.g., within the ear, nose, or throat, etc.). It should also be understood that other components of dilation instrument assembly (10) may incorporate a sensor like navigation sensor (146) of dilation catheter (140).

Dilation catheter (140) further includes a force sensor (148) along distal end (142) such that force sensor (148) is adjacent to balloon (144), tip end (143), and navigation sensor (146). Similar to navigation sensor (146), force sensor (148) is positioned distally relative to balloon (144) and proximally relative to tip end (143). Force sensor (146) is positioned along distal end (142) at an orientation relative to the position of navigation sensor (146) such that force sensor (148) is located in a similar position along distal end (142) that is separate from navigation sensor (146). The respective positions and orientations of sensors (146, 148) are interchangeable such that sensors (146, 148) may be positioned along any portion of distal end (142). Other suitable positions of sensors (146, 148) along distal end (142) will be apparent to those of ordinary skill in the art in view of the teachings herein.

Force sensor (148) is positioned on distal end (142) such that force sensor (148) is configured to respond to a force applied against distal end (142) as an operator navigates dilation catheter (140) through the anatomical passageways of a patient. By way of example only, force sensor (148) may comprise an electromechanical sensor that is operable to quantitively measure mechanical force changes at distal end (142) during the insertion of dilation catheter (140) into a patient's head. Signals generated by force sensor (148) of dilation catheter (140) may be processed by a processor (150) to determine the real-time force values experienced at distal end (142) while dilation catheter (140) is selectively maneuvered within a patient. As will be described in greater detail below, processor (150) is configured to perform interactive force measurements from the data received by force sensor (148). In other words, force sensor (148) is operable to transmit measurements of mechanical force applied to tip end (143) to processor (150) for processing and subsequent real-time display to an operator. Other suitable ways in which data from force sensor (148) may be processed and used will be apparent to those of ordinary skill in the art in view of the teachings herein.

In some versions, force sensor (148) is configured to be deformable such that sensor (148) comprises a deformable surface adapted to deform in response to a physical force pushing against sensor (148). In such versions, force sensor (148) may further include a detector operable to detect the deformation of the surface and thereby transmit the data from dilation catheter (140) to processor (150). By way of example only, the deformable surface of force sensor (148) may include a layer of elastic, deformable, or compressible material, or any other suitable material as will be apparent to those of ordinary skill in the art. In versions where force sensor (148) includes an elastic material, the elastic material may comprise an elastomer.

Figure 8:
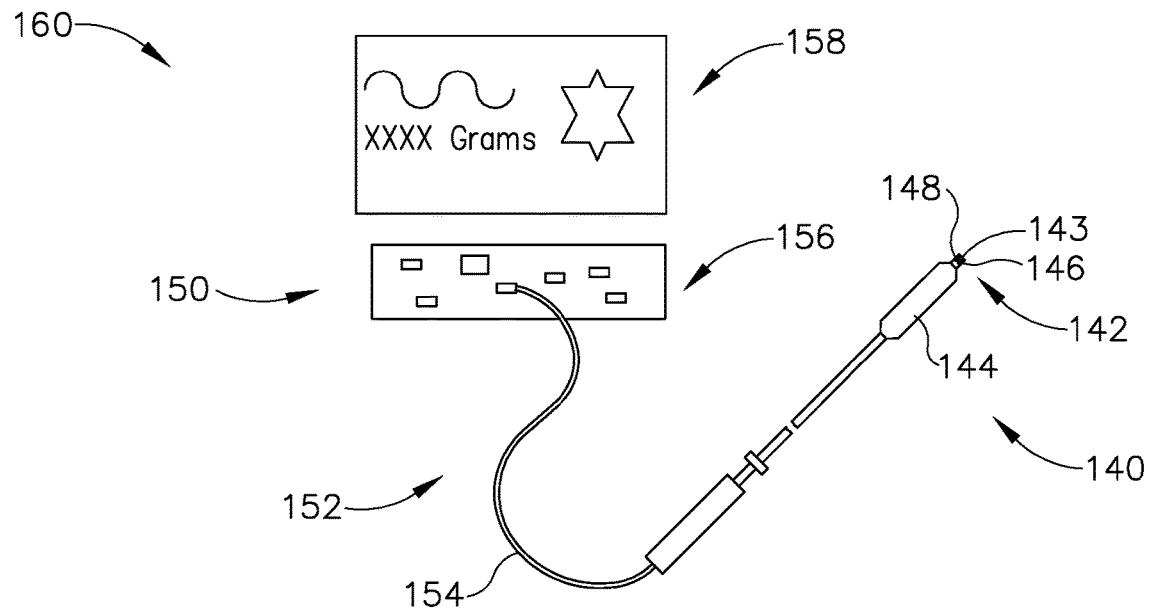
FIG. 8 depicts a schematic of an exemplary alternative sinus surgery guidance system including the dilation catheter of FIG. 6 and a computer processor system.

As shown in FIG. 8, an exemplary IGS navigation system (160) includes a processor (150). It should be understood that system (160) of the present example is configured and operable just like system (100) described above, except for the difference of including processor (150) in place of processor (110). Processor (150) of this example is configured and operable just like processor (110) except that processor (150) is further operable to receive signals from force sensor (148), in addition to signals from navigation sensor (146), and convert the signals from force sensor (148) into data representing the force encountered at distal end (142) of dilation catheter (140). Processor (150) is further configured to receive integrated anatomical information supplied from CT-scan images or other anatomical mapping data taken before a surgical procedure. Data from a preoperative CT scan or other anatomical mapping procedure is downloaded into processor (150) such that an operator is able to ascertain, in three dimensions, the precise position of sensor (146), equipped onto dilation catheter (140), at any given point in time during the procedure. This information, coupled with the visual observations provided through a standard endoscope, allows an operator to carefully position dilation catheter (140) and guidewire (30) to avoid causing damage to a nerve or other critical structures within a patient.

The other components and operability of system (160) is consistent with the teachings of system (100) described above. For example, a coupling unit (152) is configured to provide communication of data and other signals between processor (150) and dilation catheter (140), similar to coupling unit (132) described above. In this instance, however, coupling unit (152) further communicates data from force sensor (148) to processor (150). As described above, this communication of data or signals from dilation catheter (140) to processor (150) may be unidirectional, without also communicating data or other signals from processor (150). In some other versions, coupling unit (152) may provide bidirectional communication of data or other signals between dilation catheter (140) and processor (150). While coupling unit (152) of the present example couples with processor (150) through a wired coupling (154), some other versions may provide wireless communication between coupling unit (152) and processor (150). Various other suitable features and functionality that may be incorporated into coupling unit (152) will be apparent to those of ordinary skill in the art in view of the teachings herein.

Processor (150) uses software stored in a memory of processor (150) to calibrate and operate system (160) by driving field generators (306), processing data from dilation catheter (140), processing data from operating controls (156), and driving a display screen (158). The software may be downloaded to processor (150) in electronic form, over a network, for example, or it may, alternatively or additionally, be provided and/or stored on non-transitory tangible media, such as magnetic, optical, or electronic memory. Processor (150) is further operable to provide real time force values via display screen (158), showing the force encountered by force sensor (148) of dilation catheter (140) in relation to the position of distal end (142) within a patient's head.

As further seen in FIG. 8, display screen (158) outputs the data retrieved from force sensor (148), and processed by processor (150), into numerical values. By displaying real-time measurements of the force exerted on distal end (142) as dilation catheter (140) is used in a surgical procedure, display screen (158) enables an operator to analyze the current forces exhibited to thereby determine which direction to advance dilation catheter (140). Although display screen (158) displays the force data measured in grams in the present example, it should be understood that display screen (158) is operable to convert and output the data processed from processor (150) into varying measurement units, including but not limited to, kilograms (kg), pounds (lbs), newtons (N), etc., or other units of measurement as will be apparent to those of ordinary skill in the art.

As further shown in FIG. 8, display screen (158) is operable to further display the data retrieved from force sensor (148) in various other forms, a graphical representation. Although not shown, it should be understood that display screen (158) may display the data from force sensor (148) in other suitable forms as will be apparent to those of ordinary skill in the art. For instance, when force sensor (148) encounters little or no resistive force, a force feedback portion if display screen (158) may be illuminated in green. When force sensor (148) encounters an intermediate range of resistive force, a force feedback portion if display screen (158) may be illuminated in yellow. When force sensor (148) encounters substantial resistive force, a force feedback portion if display screen (158) may be illuminated in red. The colors may progressively shift among these three colors as the force traverses a range of values. Other suitable ways in which display screen (158) may provide visual feedback relating to force encountered by dilation catheter (140), based on signals from force sensor (148), will be apparent to those of ordinary skill in the art in view of the teachings herein.

Display screen (158) is operable to display the data retrieved from force sensor (148) simultaneously with the information received by navigation sensor (146) during a live surgical procedure. Such displayed content may also include graphical representations of instruments that are inserted in the patient's head, such as dilation catheter (140), such that the operator may view the virtual rendering of the instrument at its actual location in real time. As described above, such graphical representations may actually look like the instrument or may be a much simpler representation such as a dot, crosshairs, etc. By way of example only, display screen (158) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (158). The images and real-time force values provided through display screen (158) may help guide the operator in maneuvering and otherwise manipulating instruments within the patient's head.

In some instances, system (160) is operable to provide an operator with feedback when processor (150) receives data from force sensor (148) and determines that the resistive contact force encountered at distal end (142) of dilation catheter (140) exceeds a predetermined threshold. By way of example only, processor (150) may be configured to generate an audio feedback in the form of a sound or audio alert to indicate to an operator that the physical force exerted upon distal end (142) exceeds the predetermined threshold. Other suitable forms of feedback may be provided through system (160). By way of example only, system (160) may generate an optical feedback through display (158), such as a descriptive message, a lighting, or other visual cue as will be apparent to those of ordinary skill in the art. Alternatively, in some examples dilation catheter (140) is configured to generate a tactile feedback when force sensor (148) computers a force beyond the predetermined threshold. In this instance, a handle portion of dilation catheter (140) may be configured to vibrate to thereby indicate an alert to an operator. Other various forms of feedback that will be suitable for system (160) to alert an operator will be apparent to those of ordinary skill in the art in view of the teachings herein.

Figure 9:
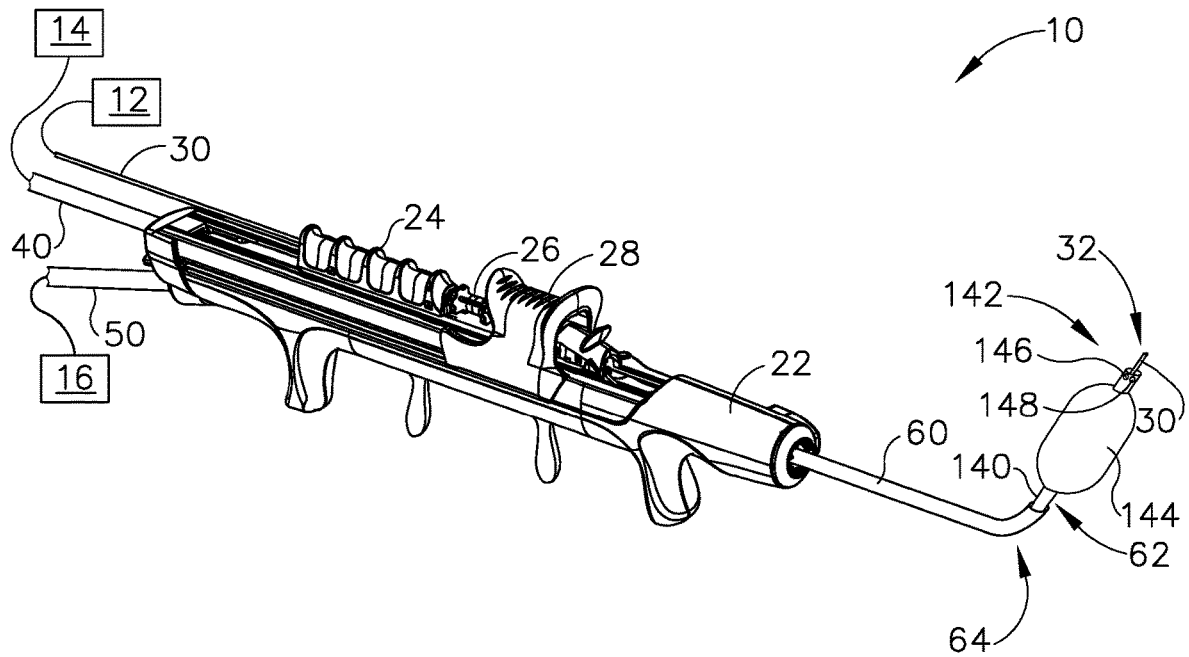
FIG. 9 depicts a perspective view of the dilation instrument assembly of FIG. 1A, with the dilation catheter of FIG. 6 slidably disposed therein, with the guidewire in a distal position, with the dilation catheter in the distal position, and with a dilator of the dilation catheter in a dilated state.

In use, dilation catheter (140) is coaxially disposed in guide catheter (60) as seen in FIG. 9. Dilation catheter slider (28) is secured to dilation catheter (140) such that translation of dilation catheter slider (28) relative to handle body (22) provides corresponding translation of dilation catheter (140) relative to handle body (22). As similarly shown in FIGS. 1B and 1C, translation of dilation catheter slider (28) from a proximal position to a distal position causes corresponding translation of dilation catheter (140) from a proximal position (FIG. 1B) to a distal position (FIG. 9). When dilation catheter (140) is in a distal position, distal end (142) of dilation catheter (140) protrudes distally from open distal end (62) of guide catheter (60). A distal portion of guidewire (30) also protrudes distally from distal end (142) of dilation catheter (140) when guidewire (30) and dilation catheter (140) are both in distal positions.

With dilation catheter (140) in the distal position relative to guide catheter (60), balloon (144), navigation sensor (146) and force sensor (148), all located adjacent to distal end (142), are extended beyond open distal end (62). Similar to balloon (44) described above, balloon (144) is in fluid communication with inflation source (14), which is configured to communicate fluid (e.g., saline, etc.) to and from balloon (144) to thereby transition balloon (144) between a non-inflated state (FIG. 1C) and an inflated state (FIG. 9). In this instance, an operator may monitor display screen (158) to navigate and view the location of distal end (142) and balloon (144) within a patient. Simultaneously, an operator may observe the pressure or force applied against distal end (142) of dilation catheter (140) as dilation catheter (140) is maneuvered within a patient's head and adjacent to various anatomical structures therein. Having the navigational and force measurements readily available, an operator may better determine when and/or where to inflate balloon (144). While not shown, it should be understood that dilation catheter (140) may further include at least two separate lumens that are in fluid isolation relative to each other. One lumen may provide a path for fluid communication between balloon (144) and inflation source (14). The other lumen may provide a path to slidably receive guidewire (30) therein.

While dilation catheter (140) of the present example is configured to transition between a non-dilated state and a dilated state based on the communication of fluid to and from balloon (144), it should be understood that dilation catheter (140) may include various other kinds of structures to serve as a dilator. By way of example only, balloon (144) may be replaced with a mechanical dilator in some other versions. Dilation catheter (140) may be constructed and operable in accordance with any of the various references cited herein. In some versions, dilator catheter (140) is configured and operable similar to the Relieva Ultirra™ Sinus Balloon Catheter by Acclarent, Inc. of Irvine, Calif. In some other versions, dilator catheter (140) is configured and operable similar to the Relieva Solo Pro™ Sinus Balloon Catheter by Acclarent, Inc. of Irvine, Calif. Other suitable variations of dilation catheter (140) will be apparent to those of ordinary skill in the art in view of the teachings herein.

Figure 10:
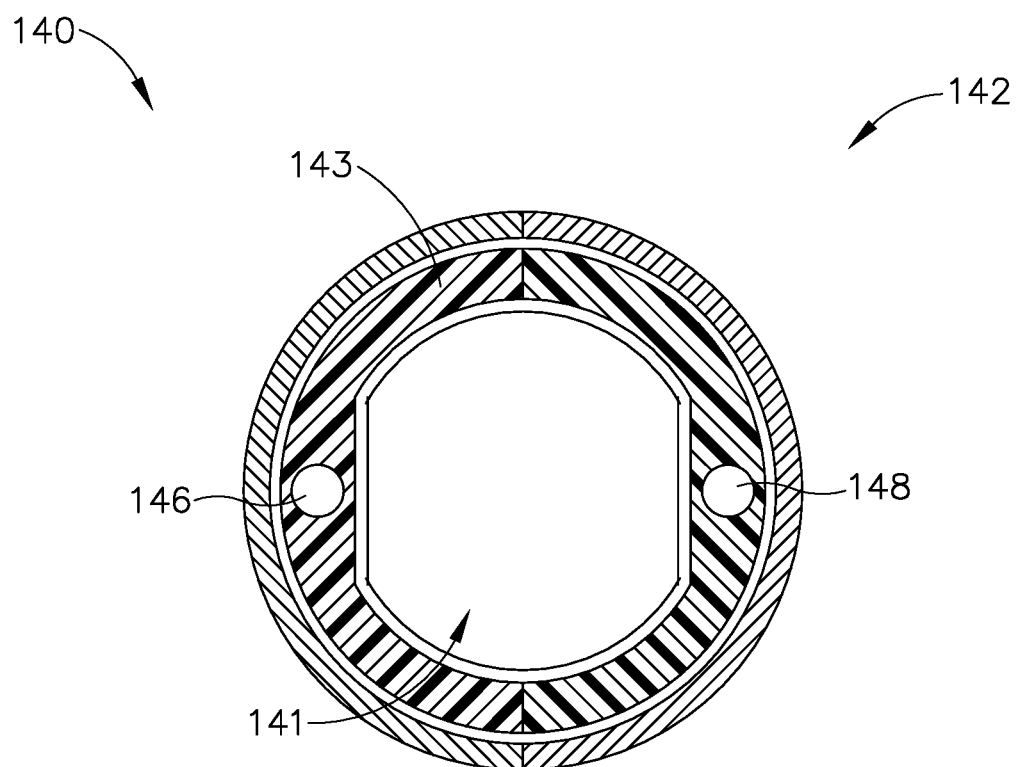
FIG. 10 depicts a cross-sectional end view of the dilation catheter of FIG. 6, with the navigation sensor and force sensor positioned on a tip of the distal end.

In some other versions, navigation sensor (146) and force sensor (148) are positioned on tip end (143) of distal end (142), as seen in FIG. 10. In this instance, rather than sensors (146, 148) being located along distal end (142) and just proximal to tip end (143), sensors (146, 148) are positioned directly at tip end (143). In this instance, both sensors (146, 148) are directed toward the same direction, distal to tip end (143), rather than in varying directions about distal end (142). Having sensors (146, 148) facing a single direction from distal end (142) may be desirable to clearly indicate to an operator the direction in which tip end (143) is facing, through the data transmitted by navigation sensor (146), and the direction which the measured force is encountered from, through the data transmitted by force sensor (148). As further seen in FIG. 10, distal end (142) further includes a lumen (141) sized and shaped to slidably receive guidewire (30) therein. It should be understood that the position and orientations of sensors (146, 148) and lumen (141) on tip end (143) may vary from those depicted in FIG. 10. Other various suitable positions and orientations of sensors (146, 148) and lumen (141) on tip end (143) will be apparent to those of ordinary skill in the art in view of the teachings herein.

While dilation catheter (140) is described above as being used with guidewire (30), dilation catheter (140) may alternatively be used with guidewire (130). In such scenarios, system (160) may provide the operator with feedback indicating the position of guidewire (130) in the head (H) of the patient (P) and also feedback indicating the position of dilation catheter (140) in the head (H) of the patient (P).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system comprising: (a) a dilation catheter, wherein the dilation catheter includes: (i) a proximal end, (ii) a distal end, (iii) a dilator, wherein the dilator is positioned proximal to the distal end, wherein the dilator is configured to transition between a non-dilated configuration and a dilated configuration, (iii) a navigation sensor positioned distal to the dilator, wherein the navigation sensor is configured to cooperate with a guidance system and thereby provide signals indicating a position of the dilation catheter in three-dimensional space, and (iv) a force sensor positioned distal to the dilator, wherein the force sensor is configured to provide signals indicating a force encountered by the force sensor; and (b) a guide member, wherein the dilation catheter is configured to slide relative to the guide member, wherein a distal portion of the guide member is sized and configured to fit in a nasal cavity of a patient.

Example 2

The system of Example 1, wherein the navigation sensor comprises an electromagnetic sensor.

Example 3

The system of any one or more of Examples 1 through 2, further comprising a sensor coupling unit, a computer processor, and a video display monitor.

Example 4

The system of Example 3, wherein the coupling unit is operable to receive the signals transmitted by the navigation sensor and force sensor, wherein the coupling unit is further operable to communicate the signals from the sensors to the computer processor.

Example 5

The system of Example 4, wherein the coupling unit is in wired communication with the computer processor.

Example 6

The system of Example 4, wherein the coupling unit is in wireless communication with the computer processor.

Example 7

The system of any one or more of Examples 4 through 6, wherein the computer processor is operable to receive the signals transmitted by the coupling unit and convert the signals into data.

Example 8

The system of Example 7, wherein the video display monitor is operable to graphically display the data converted by the computer processor, wherein the video display is further operable to display an anatomical image of the paranasal sinus.

Example 9

The system of any one or more of Examples 7 through 8, wherein the computer processor is operable to generate at least one of numerical feedback, graphical feedback, or audio feedback.

Example 10

The system of any one or more of Examples 1 through 9, further comprising a transmitter, wherein the transmitter is operable to transmit a signal that is sensed by the navigation sensor.

Example 11

The system of Example 10, wherein the transmitter comprises a generator operable to generate an electromagnetic field.

Example 12

The system of any one or more of Examples 1 through 11, wherein the guide member comprises a guide catheter.

Example 13

The system of Example 12, wherein the guide catheter defines a lumen, wherein the dilation catheter is slidably disposed in the lumen of the guide catheter.

Example 14

The system of Example 13, further comprising a guidewire, wherein the dilation catheter defines a lumen, wherein the guidewire is slidably disposed in the lumen of the dilation catheter.

Example 15

The system of any one or more of Examples 1 through 13, wherein the guide member comprises a guidewire.

Example 16

The system of Example 15, wherein the guidewire comprises a navigation sensor, wherein the navigation sensor of the guidewire is configured to cooperate with a guidance system and thereby provide signals indicating a position of the guidewire in three-dimensional space.

Example 17

A system comprising: (a) a dilation catheter, wherein the dilation catheter includes: (i) a proximal end, (ii) a distal end, (iii) a balloon dilator, wherein the balloon dilator is positioned proximal to the distal end, wherein the balloon dilator is configured to inflate from non-dilated configuration to a dilated configuration, (iii) a first sensor positioned distal to the dilator, and (iv) a second sensor positioned distal to the dilator; and (b) a guide member, wherein the dilation catheter is configured to slide relative to the guide member, wherein a distal portion of the guide member is sized and configured to fit in a nasal cavity of a patient; and (c) a processor, wherein the processor is configured to determine the position of the dilator in three-dimensional spaced based on a position signal from the first sensor, wherein the processor is further configured to determine a force exerted against the dilation catheter based on a force signal from the second sensor.

Example 18

The system of Example 17, further comprising at least one electromagnetic field generator, wherein the first sensor is configured to generate the position signal in response to movement of the first sensor within an electromagnetic field generated by the electromagnetic field generator.

Example 19

The system of any one or more of Examples 17 through 18, further comprising a display in communication with the processor, wherein the display is configured to provide visual feedback indicative of the position of the dilator in three-dimensional space, wherein the display is further configured to provide visual feedback indicative of force exerted against the dilation catheter.

Example 20

A method of navigating a medical instrument in a paranasal sinus using a guidance system, the guidance system comprising a navigation sensor, a force sensor, a processor, and a display, the method comprising: (a) advancing the medical instrument into a nasal cavity of a patient; (b) observing a position feedback indicator on a display to monitor the location of the medical instrument in the nasal cavity of the patient, wherein the position feedback indicator is rendered based on data from the navigation sensor; (c) observing a force feedback indicator on a display to monitor forces exerted against the medical instrument in the nasal cavity of the patient, wherein the force feedback indicator is rendered based on data from the force sensor; and (d) maneuvering the medical instrument in the nasal cavity in accordance with the observed feedback indicators to thereby position the medical instrument at a target site.

VI. Miscellaneous

In some versions, support assembly (300) is formed entirely of non-metallic materials. In addition, the materials used to form support assembly (300) may be configured to allow easily cleaning of support assembly (300) with disinfectants, such that the disinfectants do not damage the materials forming support assembly (300). The materials used to form any portion(s) of support assembly (300) that may come in prolonged contact with the patient's skin may also be biocompatible and comply with cytoxicity, sensitization, and irritation tests. Various suitable materials that may be used to form support assembly (300) meeting at least some of the above criteria will be apparent to those of ordinary skill in the art in view of the teachings herein.

By way of further example only, the entire weight of support assembly (300), without frame (304) and field generators (306), may be less than approximately 50 kg. Support assembly (300) may also be configured to provide sufficient mechanical support to enable the combination of chair (200) and support assembly (300) to support a patient weighing up to approximately 150 kg.

While chair (200) is provided in the examples described herein, the teachings herein may be readily used in combination with various other kinds of chairs, including but not limited to various other kinds of chairs that are designed for use in ENT procedures. Support assembly (300) may thus accommodate various kinds of backrest widths and other structural variations among chairs.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system comprising:
   (a) a dilation catheter, wherein the dilation catheter includes:
      (i) a proximal end,
      (ii) a distal end,
      (iii) a dilator, wherein the dilator is positioned proximal to the distal end, wherein the dilator is configured to transition between a non-dilated configuration and a dilated configuration,
      (iv) a navigation sensor positioned distal to the dilator, wherein the navigation sensor is configured to cooperate with a guidance system and thereby provide signals indicating a position of the dilation catheter in three-dimensional space, wherein the navigation sensor is spaced apart from the dilator by a first distance, and
      (v) a force sensor positioned distal to the dilator, wherein the force sensor is configured to provide signals indicating a force encountered by the force sensor, wherein the force sensor is spaced apart from the dilator by the first distance; and
   (b) a guide member, wherein the dilation catheter is configured to slide relative to the guide member, wherein a distal portion of the guide member is sized and configured to fit in a nasal cavity of a patient.

2. The system of claim 1, wherein the navigation sensor comprises an electromagnetic sensor.

3. The system of claim 1, further comprising a sensor coupling unit, a computer processor, and a video display monitor.

4. The system of claim 3, wherein the coupling unit is operable to receive the signals transmitted by the navigation sensor and force sensor, wherein the coupling unit is further operable to communicate the signals from the sensors to the computer processor.

5. The system of claim 4, wherein the coupling unit is in wired communication with the computer processor.

6. The system of claim 4, wherein the coupling unit is in wireless communication with the computer processor.

7. The system of claim 4, wherein the computer processor is operable to receive the signals transmitted by the coupling unit and convert the signals into data.

8. The system of claim 7, wherein the video display monitor is operable to graphically display the data converted by the computer processor, wherein the video display is further operable to display an anatomical image of the paranasal sinus.

9. The system of claim 7, wherein the computer processor is operable to generate at least one of numerical feedback, graphical feedback, or audio feedback.

10. The system of claim 1, further comprising a transmitter, wherein the transmitter is operable to transmit a signal that is sensed by the navigation sensor.

11. The system of claim 10, wherein the transmitter comprises a generator operable to generate an electromagnetic field.

12. The system of claim 1, wherein the guide member comprises a guide catheter.

13. The system of claim 12, wherein the guide catheter defines a lumen, wherein the dilation catheter is slidably disposed in the lumen of the guide catheter.

14. The system of claim 13, further comprising a guidewire, wherein the dilation catheter defines a lumen, wherein the guidewire is slidably disposed in the lumen of the dilation catheter.

15. The system of claim 1, wherein the guide member comprises a guidewire.

16. The system of claim 15, wherein the guidewire comprises a navigation sensor, wherein the navigation sensor of the guidewire is configured to cooperate with a guidance system and thereby provide signals indicating a position of the guidewire in three-dimensional space.

17. A system comprising:
   (a) a dilation catheter, wherein the dilation catheter includes:
      (i) a proximal end,
      (ii) a distal end,
      (iii) a balloon dilator, wherein the balloon dilator is positioned proximal to the distal end, wherein the balloon dilator is configured to inflate from non-dilated configuration to a dilated configuration,
      (iv) a first sensor positioned distal to the dilator and directed toward a first direction distal to the distal end, and
      (v) a second sensor positioned distal to the dilator and directed toward the first direction; and
   (b) a guide member, wherein the dilation catheter is configured to slide relative to the guide member, wherein a distal portion of the guide member is sized and configured to fit in a nasal cavity of a patient; and
   (c) a processor, wherein the processor is configured to determine the position of the dilator in three-dimensional spaced based on a position signal from the first sensor, wherein the processor is further configured to determine a force exerted against the dilation catheter based on a force signal from the second sensor.

18. The system of claim 17, further comprising at least one electromagnetic field generator, wherein the first sensor is configured to generate the position signal in response to movement of the first sensor within an electromagnetic field generated by the electromagnetic field generator.

19. The system of claim 17, further comprising a display in communication with the processor, wherein the display is configured to provide visual feedback indicative of the position of the dilator in three-dimensional space, wherein the display is further configured to provide visual feedback indicative of force exerted against the dilation catheter.

20. A method of navigating a medical instrument in a paranasal sinus using a guidance system, the guidance system comprising a navigation sensor, a force sensor, a processor, and a display, the method comprising:
(a) advancing the medical instrument into a nasal cavity of a patient;
(b) observing a position feedback indicator on a display to monitor the location of the medical instrument in the nasal cavity of the patient, wherein the position feedback indicator is rendered based on data from the navigation sensor, wherein the position feedback indicator indicates a first direction in which a distal end of the medical instrument is facing;
(c) observing a force feedback indicator on a display to monitor forces exerted against the medical instrument in the nasal cavity of the patient, wherein the force feedback indicator is rendered based on data from the force sensor, wherein the force feedback indicator indicates a second direction in which the monitored forces are exerted from; and
(d) maneuvering the medical instrument in the nasal cavity in accordance with the observed feedback indicators to thereby position the medical instrument at a target site.

* * * * *